United States Patent
Willbold et al.

(10) Patent No.: US 9,611,296 B2
(45) Date of Patent: Apr. 4, 2017

(54) PEPTIDES THAT BIND TO AMINO-TRUNCATED AMYLOID-BETA-PEPTIDE AND USE OF SAID PEPTIDES

(71) Applicant: FORSCHUNGSZENTRUM JUELICH GMBH, Juelich (DE)

(72) Inventors: Dieter Willbold, Juelich (DE); Susanne Aileen Funke, Sonnefeld (DE); Yeliz Cinar, Wiesbaden (DE); Dirk Bartnik, Cologne (DE); Hans-Ulrich Demuth, Halle/Saale (DE); Martin Kleinschmidt, Halle/Saale (DE); Hans-Henning Ludwig, Halle/Saale (DE)

(73) Assignee: Forschungszentrum Juelich GmbH, Juelich (DE)

( * ) Notice: Subject to any disclaimer, the term of this patent is extended or adjusted under 35 U.S.C. 154(b) by 14 days.

(21) Appl. No.: 14/439,895

(22) PCT Filed: Sep. 25, 2013

(86) PCT No.: PCT/DE2013/000543
§ 371 (c)(1),
(2) Date: Apr. 30, 2015

(87) PCT Pub. No.: WO2014/067505
PCT Pub. Date: May 8, 2014

(65) Prior Publication Data
US 2015/0284432 A1 Oct. 8, 2015

(30) Foreign Application Priority Data
Nov. 2, 2012 (DE) .................. 10 2012 022 013

(51) Int. Cl.
*C07K 7/08* (2006.01)
*G01N 33/68* (2006.01)

(52) U.S. Cl.
CPC ........... *C07K 7/08* (2013.01); *G01N 33/6896* (2013.01); *G01N 2333/4709* (2013.01)

(58) Field of Classification Search
CPC ...... C07K 16/18; C07K 14/4711; C07K 7/08; G01N 33/6896; G01N 2333/4709; G01N 2800/2814; G01N 2800/387; G01N 2800/28

See application file for complete search history.

(56) References Cited

U.S. PATENT DOCUMENTS 4,782,227 A 11/1988 Micheron et al.
2011/0008008 A1 1/2011 Chowdhury et al.

FOREIGN PATENT DOCUMENTS

| CN | 101084581 | 12/2007 |
|----|-----------|---------|
| EP | 0 661 754 | 7/1995 |
| EP | 1 379 546 | 1/2004 |
| WO | WO-2007/121265 | 10/2007 |
| WO | WO-2012/136552 | 10/2012 |

OTHER PUBLICATIONS

Van Groen et al., ChemMedChem 2009, 4, 276-282 In vitro and in vivo Staining Characteristics of Small, Fluorescent, Aβ42-Binding D-Enantiomeric Peptides in Transgenic AD Mouse Models.

Katja Wiesehan et al: "Selection of D-Amino-Acid Peptides That Bind to Alzheimer's Disease amyloid Peptide A[beta]142 by Mirror Image Phage Display" Chembiochem, Bd. 4, Nr. 8, Aug. 4, 2003 (Aug. 4, 2003), Seiten 748-753, XP055069247, ISSN: 1439-4227, DOI: 10.1002/cbic.200300631 Seite 749, rechte Spalte—Seite 751, Iinke Spalte; Tabelle 1.

Mamikonyan, G.; [u.a.]: Anti-Aβ1-11antibody binds to different β-Amyloid species, inhibits fibril formation, and disaggregates preformed fibrils but not the most toxis oligomers, 2007. In: J. Biol. Chem., vol. 282, S. 22376-22386.

*Primary Examiner* — Gregory S Emch
(74) *Attorney, Agent, or Firm* — Jordan and Koda, PLLC

(57) ABSTRACT

Peptides that bind to amino-terminal truncated pEAβ3-42, the free glutamic acid residue of which lies in position 3 or 11 in the form of cyclized pyroglutamate. Four oligopeptides were identified using mirror image phage display technology.

16 Claims, 1 Drawing Sheet

| D1 | D4 | D5 | D6 | D7 |
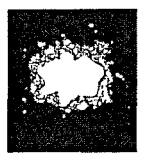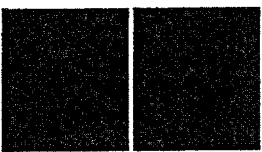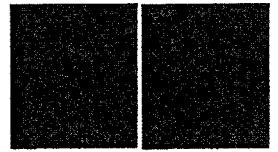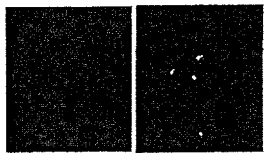
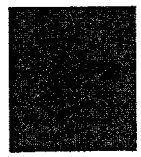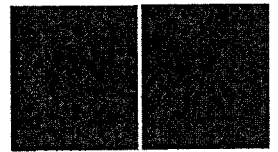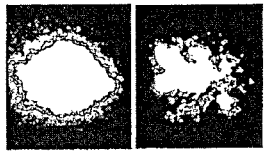

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: D7 - Peptid

<400> SEQUENCE: 1

His Thr Arg Phe Glu Tyr Tyr Val Tyr His Met Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: D6 - Peptid

<400> SEQUENCE: 2

Ala Gly Glu Arg Leu Lys Phe Ile Asp Glu His Val
1               5                   10

<210> SEQ ID NO 3
<211> LENGTH: 12
<212> TYPE: PRT
<213> ORGANISM: Artificial Sequence
```

```
<220> FEATURE:
<223> OTHER INFORMATION: D4 - Peptid

<400> SEQUENCE: 3

Lys Met Glu His Pro Asn His Pro Pro Pro Gln Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: D5 - Peptid

<400> SEQUENCE: 4

Asn Gly Ala Pro Asn Lys Ile Pro Arg Asp Arg Glu
1               5                   10
```

PEPTIDES THAT BIND TO AMINO-TRUNCATED AMYLOID-BETA-PEPTIDE AND USE OF SAID PEPTIDES

The invention relates to peptides that bind to amino-terminal truncated amyloid-beta peptide (AβpE3-x) and to the use of said peptides.

BACKGROUND OF THE INVENTION

Alzheimer's dementia (AD) is the most common form of dementia and affects around 20 million people worldwide. The main pathological feature of AD is the formation of senile or amyloid plaques, consisting of Aβ peptide (amyloid-beta peptide, A-Beta peptide), and neurofibrillary deposits of the tau protein. The amyloid cascade hypothesis came about in the 1990s and postulates that the deposition of Aβ in the form of plaques triggers the symptoms of the disease. More recent studies indicate that smaller, freely diffusible Aβ oligomers are more toxic than the Aβ fibrils deposited in the plaques. According to recent work, the plaques can be regarded as a reservoir for oligomeric Aβ, which is colocalized with the destruction of synapses and neurons. Aβ peptide is created by the activities of at least two different proteases from a precursor protein, the "Amyloid Precursor Protein" (APP). This is located in the cell wall of neurons. During the proteolytic breakdown of APP and by subsequent modification, Aβ fragments of varying lengths and types are produced. After digestion by gamma-secretase, Aβ peptides of varying lengths are formed, for example Aβ 1-42, Aβ 1-40, and so on. These species differ in their tendency to aggregate. In addition, it is known that some of the Aβ species found in the human brain can no longer be detected as the original peptide but rather as truncated AβpE3-x. AβpE3-x denotes amino-terminal truncated peptides, the free glutamic acid residue of which lies in position 3 in the form of cyclized pyroglutamate. The C-terminus is variable, for example AβpE3-40, AβpE3-42, and so on. AβpE3-x, especially AβpE3-42, is largely detected in the center of amyloid plaques and is much more likely to aggregate and much more toxic to cells than non-amino-terminal truncated and modified Aβ.

There is therefore a need for substances that reduce the quantity of toxic Aβ oligomers and/or truncated and modified Aβ species.

To date, no medicament exists that acts on the cause of Alzheimer's dementia. The medicaments used to date are at best able to alleviate some symptoms, but are unable to slow, far less stop, the progress of the disease.

Disadvantageously it has, therefore, been possible to treat only the symptoms of Alzheimer's dementia to date. There are no approved medicaments that can stop or reverse the disease processes. Most of the substances researched for treating Alzheimer's dementia focus on extracellular Aβ but do not focus specifically on soluble Aβ oligomers or on truncated Aβ species such as AβpE3-42 that are likely to aggregate. However, this is precisely what is required in order to be able to stop the disease process in the early stages.

Furthermore, there is to date no way of diagnosing Alzheimer's dementia before the appearance of symptoms. At present Alzheimer's dementias are detected mainly through neuropsychological tests carried out on a person already suffering from dementia symptoms. Other diseases (traumas) can moreover be ruled out by different investigative methods. However, it is known that Aβ oligomers and then plaques appear in the brain of patients and cause irreversible damage up to 20 years prior to the onset of symptoms.

Molecular probes which are injected intravenously into the patient and which bind to Aβ oligomers and plaques after crossing the blood/brain barrier could be made visible by means of imaging methods and could thus enable earlier diagnosis of Alzheimer's dementia.

To date, no probes for in-vivo imaging methods exist that bind specifically to pyro-Glu-Aβ species and make the latter visible. Since pyro-Glu-Aβ oligomers play such an important and early role in the disease history, this is precisely what is needed.

SUMMARY OF THE INVENTION

The problem addressed by the invention is that of providing new candidates for
A) treating the cause of Alzheimer's disease
and for
B) detecting Alzheimer's dementia at the early stage of onset.

The problem is solved by the peptide according to the main claim.

According to the invention, the problem addressed by the invention is solved by peptides that bind to amino-terminal truncated Aβ peptide, the free glutamic acid residue of which lies in position 3 in the form of cyclized pyroglutamate (AβpE3-x).

It has been found that such peptides are able to suppress the formation of toxic Aβ oligomers or aggregates. The peptides advantageously bind to truncated amyloid-β peptide that is found in the body, which is to say to AβpE3-x, in particular to the pE3-42 species. The binding of the peptide to the monomeric form prevents the formation of toxic aggregates. The binding to the oligomeric form dissolves these back into non-toxic monomers or detoxifies them by transforming them into non-toxic aggregates. As a result, a detoxification is advantageously ensured by the binding of peptide to truncated amyloid-β peptide (AβpE3-x).

Furthermore, the peptides are advantageously used as probes for use in imaging methods, such as, for example, Positron Emission Tomography (PET) or Single Photon Emission Computed Tomography (SPECT).

The present invention therefore also relates to the use of the peptides as probes for identifying Aβ oligomers, particularly truncated Aβ oligomers or truncated Aβ monomers (plaques).

Such probes are highly important since they enable early diagnosis of Alzheimer's dementia. Actions can thus already be taken against the disease at a very early stage.

Such molecular probes contain the peptide according to the invention and can be injected into the patient, for example intravenously. Further constituents of the probe may be: dyes, fluorescent dyes, radioactive isotopes (for example for PET), gadolinium (for MRI) and/or constituents which are used for probes in imaging. After crossing the blood/brain barrier, the probes can bind to the Aβ oligomers and/or plaques. The truncated Aβ oligomers and/or plaques of truncated Aβ oligomers labelled in this way can be made visible by means of imaging methods such as, for example, SPECT, PET, CT, MRT, proton MR spectroscopy, etc., specifically also in vivo.

The present invention also relates to the use of the peptide for preventing the multiplication of particularly toxic, truncated Aβ oligomers (AβpE3-x).

The peptides according to the invention can also be used to form non-toxic peptide/Aβ-oligomer complexes.

With particular advantage, the peptides according to the invention consist predominantly or exclusively of D-enantiomeric amino acids.

Hereinbelow, the term "predominantly of D-enantiomeric amino acids" means that the monomers to be used are composed of D-amino acids in a proportion of at least 80%, preferably 75%, 80%, particularly preferably 85%, 90%, 95%, in particular 96%, 97%, 98%, 99%, 100%.

The D-enantiomeric peptides can advantageously be produced synthetically and in general do not occur naturally. Relative to L-enantiomeric peptides, they behave as image and mirror image. They can be obtained by mirror image phage display technology.

Enzymes occurring in the body, such as proteases for example, or immune system proteins advantageously do not recognize the D-enantiomeric peptides. In vivo, therefore, the latter are more resistant to proteases than L-enantiomeric peptides and cause only a weak immune response, if any. This advantageously significantly reduces the risk of side effects.

In a mirror image phage display selection, a total of four new D-enantiomeric peptides were selected that bind principally to truncated AβpE3-x.

Four different dodecameric D-peptides (one-letter code) were selected and were identified as new candidates for solving the problem.

```
D7      HTRFEYYVYHMS according to SEQ ID NO: 1

D6      AGERLKFIDEHV according to SEQ ID NO: 2

D4      KMEHPNHPPPQR according to SEQ ID NO: 3
and

D5      NGAPNKIPRDRE according to SEQ ID NO: 4.
```

These were derived from the selected mirror-image L-peptides. D4 and D5 had aggregation-nucleus-free prepared AβpE3-x as the selection target; D8 and D7 respectively had low-molecular-weight or high-molecular-weight AβpE3-x aggregates.

With particular advantage, the structures according to one of the sequences having SEQ ID NO:1, SEQ ID NO:2, SEQ ID NO:3 or SEQ ID NO:4 or a mixture thereof are new candidates for therapeutic agents for treating Alzheimer's dementia.

With particular advantage, the structures are also new candidates for detecting Alzheimer's dementia and the plaques associated therewith.

The method for detecting plaques that consist at least partially of amino-terminal truncated Aβ peptides (AβpE3-x)(the free glutamic acid residue of which lies in position 3 in the form of cyclized pyroglutamate, takes place with the following steps:
  bringing the plaques into contact with a labelled peptide or a probe that binds to the amino-terminal truncated Aβ peptide; and
  detecting the plaques by means of an imaging method.

The method provides for assessing the images outside of the body by comparison with images from healthy test subjects. The defection of plaques even in vivo is thus advantageously made possible.

With particular advantage, use is made of peptides that consist predominantly or exclusively of D-enantiomeric amino acids.

In one embodiment of the invention, the method is characterized by selecting a peptide having one of the sequences having SEQ ID NO:1, SEQ ID NO:2, SEQ ID NO:3 or SEQ ID NO:4 or a mixture thereof.

BRIEF DESCRIPTION OF THE DRAWINGS

FIG. 1 shows histological staining of plaques in the brain (cortex) of transgenic Alzheimer mice (Tg2576), which express the human Aβ precursor protein, with the D-enantiomeric peptides D4, D5, D6 and D7.

DESCRIPTION OF THE PREFERRED EMBODIMENTS

The invention will be described in more detail below on the basis of an exemplary embodiment and the appended figure, without this being intended to limit the invention in any way.

The D-enantiomeric peptides having SEQ ID NO: 1-4 were obtained as follows.

In a mirror image phage display selection, a total of four new D-enantiomeric peptides were selected that bind principally to truncated AβpE3-x. Synthetically produced AβpE3-x was used as the target molecule in different mirror image phage display selection processes. The phage display method makes it possible to select, from a very large library of different peptides, those peptides that bind to a specific target molecule. To this end, the peptides are displayed on bacteriophages. Mirror image phage display is a special type of phage display. In phage display, the L-enantiomeric target protein is used as the target in the selection. The phages display a peptide library on their surface and the phages that display the binding partner for the target molecule ("target") are enriched by iterative rounds of binding, washing and amplification. In mirror image phage display, the mirror image of the actual target is used. L-enantiomeric peptides which bind to the mirror image of the target molecule are then selected by phage display. The mirror image of the L-peptide thus identified (identical amino acid sequence but all amino acids consist of D-enantiomers) then binds to the actual, original target molecule. The selections in the mirror image phage display were carried out against AβpE3-x without aggregation nuclei, which is to say mainly monomers, in low-molecular-weight and high-molecular-weight aggregate form.

To prepare high-molecular-weight aggregates of pyroglutamate-Aβ, AβpE3-38-Bio (Bio: biotin, for immobilizing the peptides for selection on streptavidin microtiter plates) and AβpE3-40 were diluted to 10 and 100 μM respectively in hexafluoroisopropanol (HFIP). The two peptides were then jointly aliquoted to 15 μg at a ratio of 1:20. To prepare high-molecular-weight aggregates, the peptide film was dissolved in 5 μl of dimethyl sulfoxide and taken up in 95 μl of physiological buffer PBS (140 mM NaCl; 2.7 mM KCl; 10 mM $Na_2HPO_4$, pH 7.4). Incubation then took place at 37° C. and 500 rpm for 3 days, followed by immobilization for 1 hour. To prepare low-molecular-weight aggregates, use was again made of AβpE3-38-Bio and AβpE3-40. First, 871 ng of AβpE3-38-Bio as the peptide film was dissolved in NaOH and taken up in sodium phosphate buffer pH 7.4 (NaPi) and aliquoted to 87 ng per well. After immobilization for 20 minutes, the solution was removed and discarded. Then, 871 ng of AβpE3-40 was likewise dissolved in NaOH and taken up in 250 μl of NaPi, added to the pre-immobilized well and immobilized for a further 2 hours. To prepare peptides without aggregation nuclei, the 1 mM stock solution of AβpE3-38-Bio was further diluted in HFIP to 1 µM and aliquoted to in each case 871 ng.

After HFIP had evaporated off overnight, the peptide film was dissolved in 53 µl of NaOH, 947 µl of NaPi were added and in each case 100 µl containing 87 ng Aβ were pipetted into the wells. This was followed by immobilization for 30 minutes.

In the mirror image phage display selection, new D-enantiomeric peptides were selected that ought to bind principally to truncated pEAβ3-x. The selections in the mirror image phage display were carried out against AβpE3-x without aggregation nuclei, which is to say mainly monomers, in low-molecular-weight and high-molecular-weight aggregate form. Four different dodecameric D-peptides D4 (KMEHPNHPPPQR according to SEQ ID NO:3), D5 (NGAPNKIPRDRE according to SEQ ID NO:4), D6 (AGERLKFIDEHV according to SEQ ID NO:2) and D7 (HTRFEYYVYHMS according to SEQ ID NO:1) were derived from the selected mirror-image L-peptides. D4 and D5 had aggregation-nucleus-free prepared AβpE3-x as the selection target; D6 and D7 respectively had low-molecular-weight or high-molecular-weight AβpE3-x aggregates.

The binding properties of the available peptides to Aβ plaques were investigated. For staining frontal brain slices, use was made of preparations of transgenic Tg2576 mice aged from 10 to 11 months, which due to the human APP gene bearing the Swedish mutation have an increased Aβ 1-42 expression and plaque formation. In these mice, it was also possible to detect AβpE3-x as a plaque constituent.

For the tests, the peptides were synthetically produced and labelled by a commercial supplier, A test was then carried out, ex vivo, to determine the regions of the plaques to which binding had mainly taken place. It must be assumed here that Aβ plaques consist of different Aβ species, such as, for example, Aβ1-40, 1-42 and AβpE3-x.

The results are shown in FIG. 1.

All the peptides are combined with fluorescein isothiocyanate (FITC) for detection by means of fluorescence microscopy. The D1-FITC peptide, which binds Aβ plaques (specifically Aβ 1-42) (Wiesehan et al., ChemBioChem 2003, 4, 748-753; Van Groen et al., ChemMedChem 2009, 4, 276-282), was used as positive control.

As a further control, the same tests were carried out after Congo red staining, which served to verify the plaque structures (bottom image in each case). It must be assumed that the plaques are composed of different Aβ isoforms (Aβ 1-40, 1-42, AβpE3-x). Slices from wild-type animals without plaque formation were also treated. In these tests, no Congo red or fluorescein fluorescence could be detected (data not shown).

In the brain slices treated with D4, D5 and D6, only plaques having a relatively dense structure, consisting of Aβ fibrils, were stained, but not small and diffuse plaques consisting of amorphous Aβ aggregates. Furthermore, ring-shaped structures around the inner core of the plaques were stained more intensely. D7 likewise stained only dense structures but, unlike the other peptides, at the inner core of the plaques. This indicates that a specific distribution of the different Aβ isoforms was possibly detected by the D-peptides in the plaques.

The selected D-peptides D4, D5, D8 and D7 are thus candidates of interest according to the invention for developing biomolecular plaque probes and for the use thereof in diagnostic detection methods. The selective and possibly specific affinity for different plaque structures and Aβ isoforms could aid the diagnosis of Alzheimer's dementia in imaging methods and could be used to differentiate this from other amyloid-associated neurodegenerative diseases. The peptides can be used for therapeutic purposes. To date, no peptides are known which are generated in a selection against pEAβ and which could be used for diagnostic and therapeutic purposes.

The invention claimed is:

1. A D-enantiomeric peptide, comprising a sequence selected from the group consisting of: SEQ ID NO:1, 2, 3, 4 and a mixture thereof:
   wherein said D-enantiomeric peptide, at a sequence portion consisting of one of said SEQ ID NO: 1, 2, 3, and 4 binds to amino-terminal truncated amyloid-beta peptide; and
   wherein said amino-terminal truncated amyloid-beta peptide is a species of amino-terminal truncated amyloid-beta peptide having a free glutamic acid residue in position 3 in the form of cyclized pyroglutamate.

2. The D-enantiomeric peptide according to claim 1, wherein the sequence is comprised of D-enantiomeric amino acids.

3. The D-enantiomeric peptide according to claim 2, wherein the D-enantiomeric peptide is comprised of at least 60% D-enantiomeric amino acids.

4. The D-enantiomeric peptide according to claim 1, for use in medicine.

5. The D-enantiomeric peptide according to claim 1, for treatment of Alzheimer's disease.

6. A therapeutic agent for treating Alzheimer's disease comprising the D-enantiomeric peptide according to claim 1.

7. The therapeutic agent according to claim 6, wherein the D-enantiomeric peptide is comprised of D-enantiomeric amino acids.

8. A D-enantiomeric peptide comprising a sequence selected from the group consisting of SEQ ID NO:1, 2, 3, 4 and a mixture thereof.

9. The D-enantiomeric peptide of claim 8, wherein the peptide consists of a sequence selected from the group consisting of SEQ ID NO:1, 2, 3, 4 and a mixture thereof.

10. A therapeutic agent for treating Alzheimer's disease comprised of the D-enantiomeric peptide according to claim 8.

11. The D-enantiomeric peptide according to claim 8, wherein the D-enantiomeric peptide is comprised of at least 60% D-enantiomeric amino acids.

12. A probe comprising a D-enantiomeric peptide according to claim 1.

13. A probe comprising a D-enantiomeric peptide according to claim 1 for identifying amyloid-beta oligomers.

14. A probe comprising a D-enantiomeric peptide according to claim 1 for preventing amyloid-beta oligomers.

15. A method for detecting plaques that include amino-terminal truncated amyloid-beta peptides, the free glutamic acid residue of which lies in position 3 in the form of cyclized pyroglutamate, comprising the steps of:
   contacting the plaques with a labelled D-enantiomeric peptide or a probe that binds to the amino-terminal truncated amyloid-beta peptide at a portion of the D-enantiomeric peptide consisting of a sequence selected from the group consisting of SEQ ID NO. 1, 2, 3 and 4; and
   detecting the plaques by means of an imaging method.

16. The method according to claim 15, wherein the peptide sequence is comprised of D-enantiomeric amino acids.

* * * * *